United States Patent
Escaich Ferrer et al.

(10) Patent No.: US 7,943,598 B2
(45) Date of Patent: May 17, 2011

(54) USE OF ORGANIC GLUCOSAMINE SALTS

(75) Inventors: Josep Escaich Ferrer, Barcelona (ES); Ramon Ruhi Roura, Barcelona (ES); Ana Maria Torrent Gibert, Massanes (ES)

(73) Assignee: Bioiberica, S.A., Barcelona (ES)

( * ) Notice: Subject to any disclaimer, the term of this patent is extended or adjusted under 35 U.S.C. 154(b) by 1136 days.

(21) Appl. No.: 11/659,504

(22) PCT Filed: Jun. 23, 2005

(86) PCT No.: PCT/EP2005/006804
§ 371 (c)(1),
(2), (4) Date: Feb. 6, 2007

(87) PCT Pub. No.: WO2006/012951
PCT Pub. Date: Feb. 9, 2006

(65) Prior Publication Data
US 2007/0244070 A1    Oct. 18, 2007

(30) Foreign Application Priority Data
Aug. 6, 2004 (ES) .................................. 200401972

(51) Int. Cl.
*A01N 43/04* (2006.01)
*A61K 31/70* (2006.01)

(52) U.S. Cl. ......................................................... 514/62
(58) Field of Classification Search .................. None
See application file for complete search history.

(56) References Cited

U.S. PATENT DOCUMENTS
3,683,076 A * 8/1972 Rovati et al. .................... 514/62
2004/0092482 A1 5/2004 Gupta FOREIGN PATENT DOCUMENTS
| EP | 0 444 000 | 8/1991 |
| EP | 1238669 A2 | 9/2002 |
| JP | 2002-187846 A | 7/2002 |
| RU | 2118156 C1 | 8/1998 |

OTHER PUBLICATIONS
Dodge et al, *Osteoarthritis and Cartilage*, 11(6):424-432 (2003).

* cited by examiner

*Primary Examiner* — Traviss C McIntosh, III
(74) *Attorney, Agent, or Firm* — Sughrue Mion, PLLC

(57) ABSTRACT

The present invention relates to the use of an organic glucosamine salt selected from glucosamine glucuronate, glucosamine ascorbate, glucosamine malate, glucosamine hydrogen malate, glucosamine citrate, glucosamine hydrogen citrate, and glucosamine dihydrogen citrate for the preparation of a medicament for the treatment of arthrosis and inflammation and pain associated with arthrosis. The present invention also relates to the use of an organic glucosamine salt, selected from the ones mentioned above, for the preparation of a nutritional supplement acting as a chondroprotector, to nourish the cartilage, protect the joints, prevent water deficit in the tissues that form the joint, improve the joints' functional capacity, elasticity, and flexibility, and prevent and revert the physical overexertion syndrome in athletes, and the effects associated therewith.

8 Claims, 1 Drawing Sheet

USE OF ORGANIC GLUCOSAMINE SALTS

This application is a 371 of PCT/EP2005/006804, filed Jun. 23, 2005; the disclosure of which is incorporated herein by reference.

TECHNICAL FIELD OF THE INVENTION

This invention relates to the use of an organic glucosamine salt for the treatment or prophylaxis of arthrosis, of the inflammation associated with arthrosis, and the pain associated with arthrosis. Likewise, this invention relates to the use of an organic glucosamine salt for the preparation of a nutritional supplement acting as a chondroprotector, as a cartilage nutrient, as a joint protector, to prevent water deficit in the tissues that form the joints, to improve the joints' functional capacity, elasticity, and flexibility, and for the prophylaxis and reversion of the physical overexertion syndrome in athletes and the undesirable effects associated therewith.

DESCRIPTION OF THE PRIOR ART

Arthrosis, also known as osteoarthritis, is a degenerative joint disease which affects most people over 65 years of age, characterized by a gradual degradation of the cartilaginous tissue, together with the presence of inflammation and pain. Synovial inflammation normally appears later, when the disease is at an advanced stage and is different in nature from the inflammation observed in rheumatoid arthritis, and generally is only a minority component of arthrosic pathology. Arthrosis may be defined as the degeneration of the hyaline articular cartilage. A secondary effect thereto is affectation of the synovial membrane and the subohondral bone, as well as the formation of new bone on the margins of the joint surfaces. The etiology of arthrosis is unknown and its evolution is slow. Depending on its etiology, arthrosis may be divided into two groups. The first would be primary arthrosis, wherein the cartilage begins to degenerate and become injured without a known cause having been determined, and secondary arthrosis, which is related to the presence of mechanical alterations or problems in the joint, with wounds, infections, metabolic disorders, or other dysfunctions. However, a series of risk factors for the appearance of the disease have been described, such as: ageing, inheritance, obesity, overloading disorders, physical overexertion in athletes, injuries or traumas, bone mineral density, among others.

The cartilage allows bones to move, slipping over one another. It also absorbs the stress produced by physical movement. In arthrosis, the surface of the cartilage breaks and wears out, causing bones to move against one another, which leads to friction, pain, swelling, and loss of joint movement. As time goes on, the joint may deform.

Under normal conditions, cartilage renewal is a very slow process, which consists of a constant synthesis (anabolism) and degradation (catabolism) of the extracellular matrix components. The chondrocyte is the cell responsible for this metabolism, which must be coordinated.

Under pathological conditions, this process is altered, because cartilage renewal is accelerated, which leads to a precocious repair of the cartilaginous tissue caused by an imbalance between the chondrocyte's anabolic and catabolic programmes, which entails degradation of the cartilage. The repair reaction is the result of a hyperproliferation of chondrocytes, together with an increase in the synthesis of the cartilage's extracellular matrix components by these cells (D. Hamermam et al., *N. Engl. J. Med.*, 320, 1322-1330 (1989)). Consequently, there exists a balance between synthesis and degradation of the cartilage which controls this homeostatic reaction and which depends on systemic hormones and growth factors whose secretions decrease with age. Cartilage degradation is regulated by enzymes and free radicals produced by adjacent tissues, but also by the chondrocyte itself.

We will highlight the following current pharmacological treatments for arthrosis:

Symptomatic-action substances which have a rapid action, such as analgesics, non-steroidal anti-inflammatory drugs (NSAIDs), corticoids, and cyclo-oxygenase 2 inhibitors (COX-2). The use of some of them entails a high risk of potentially severe secondary effects, such as gastrointestinal problems in the case of NSAIDs.

Symptomatic-action substances which act in a slower manner, known as SYSADOA (Symptomatic Slow Acting Drug for Osteoarthritis) (M. G. Lequesne, *Rev. Rhum.* (Eng./Ed.), 61, 69-73 (1994)), include hyaluronic acid, chondroitin sulphate, glucosamine hydrochloride, and the so-called glucosamine sulphate. This group is characterized by having as additional advantages a greater safety by comparison with NSAIDs and a more prolonged action, of even several months after the suppression of treatment.

Glucosamine, which is an aminomonosaccharide, is an intermediate substrate used by the joint cartilage in the synthesis of glycosaminoglycans and proteoglycans. Glucosamine is present as a natural compound in almost all human tissues.

Various research groups are still studying the effects of glucosamine hydrochloride on arthrosis. H. Nakamura et al. (*Clin. Exp. Rheumatol.* 22 (3), 293-9, (2004)) describe the effects of glucosamine hydrochloride in the production of prostaglandin E2, nitric oxide, and metalloproteases by chondrocytes and synoviocytes in arthrosis. These researchers conclude that glucosamine hydrochloride modulates the metabolism of chondrocytes and synoviocytes.

Some researchers looked for an alternative to the use of glucosamine hydrochloride in the treatment of arthrosis, by attempting to stabilize glucosamine sulphate, either by adding other components (EP 444,000 B1) or by forming the so-called mixed salts (WO 99/61455).

From all of the above, one may conclude that providing other glucosamine salts as an alternative to the glucosamine hydrochloride salt in the treatment of arthrosis and other conditions associated with arthrosic pathology, as well as for the preparation of nutritional supplements to act on the cartilage, the joints, and the undesirable effects produced by physical overexertion in athletes is still a therapeutic and nutritional problem.

Until now no description has been found of the use of glucosamine glucuronate, glucosamine ascorbate, glucosamine malate, glucosamine hydrogen malate, glucosamine citrate, glucosamine hydrogen citrate, or glucosamine dihydrogen citrate in the treatment or prophylaxis of arthrosis, the inflammation associated with arthrosis or the pain associated with arthrosis.

We also have not found any description of the use of glucosamine glucuronate, glucosamine ascorbate, glucosamine malate, glucosamine hydrogen malate, glucosamine citrate, glucosamine hydrogen citrate, or glucosamine dihydrogen citrate for the preparation of a nutritional supplement to act as a chondroprotector, as a cartilage nutrient, or to act as a joint protector or in the prophylaxis and reversion of water deficit in the tissues which form the joint or in order to enhance the joints' functional capacity, elasticity, and flexibility, or in the prophylaxis and reversion of the physical overexertion syndrome in athletes and the undesirable effects associated therewith, particularly bone, joint, muscle, and cartilage injuries.

DISCLOSURE OF THE INVENTION

The present invention relates to the use of an organic glucosamine salt selected from the group consisting of glucosamine glucuronate, glucosamine ascorbate, glucosamine malate, glucosamine hydrogen malate, glucosamine citrate, glucosamine hydrogen citrate, and glucosamine dihydrogen citrate, for the preparation of a medicament for the treatment, prevention, or prophylaxis of arthrosis in a mammal.

Another aspect of the present invention is the use of an organic glucosamine salt selected from the group consisting of glucosamine glucuronate, glucosamine ascorbate, glucosamine malate, glucosamine hydrogen malate, glucosamine citrate, glucosamine hydrogen citrate, and glucosamine dihydrogen citrate, for the preparation of a medicament for the treatment of inflammation associated with arthrosis in a mammal.

Another aspect of the present invention is the use of an organic glucosamine salt selected from the group consisting of glucosamine glucuronate, glucosamine ascorbate, glucosamine malate, glucosamine hydrogen malate, glucosamine citrate, glucosamine hydrogen citrate, and glucosamine dihydrogen citrate, for the preparation of a medicament for the treatment of pain associated with arthrosis in a mammal.

Another aspect of the present invention is the use of an organic glucosamine salt selected from the group consisting of glucosamine glucuronate, glucosamine ascorbate, glucosamine malate, glucosamine hydrogen malate, glucosamine citrate, glucosamine hydrogen citrate, and glucosamine dihydrogen citrate, for the preparation of a nutritional supplement to act as a chondroprotector.

Another aspect of the present invention is the use of an organic glucosamine salt selected from the group consisting of glucosamine glucuronate, glucosamine ascorbate, glucosamine malate, glucosamine hydrogen malate, glucosamine citrate, glucosamine hydrogen citrate, and glucosamine dihydrogen citrate, for the preparation of a nutritional supplement to act as a cartilage nutrient.

Another aspect of the present invention is the use of an organic glucosamine salt selected from the group consisting of glucosamine glucuronate, glucosamine ascorbate, glucosamine malate, glucosamine hydrogen malate, glucosamine citrate, glucosamine hydrogen citrate, and glucosamine dihydrogen citrate, for the preparation of a nutritional supplement to act as a joint protector.

Another aspect of the present invention is the use of an organic glucosamine salt selected from the group consisting of glucosamine glucuronate, glucosamine ascorbate, glucosamine malate, glucosamine hydrogen malate, glucosamine citrate, glucosamine hydrogen citrate, and glucosamine dihydrogen citrate, for the preparation of a nutritional supplement for the prophylaxis and reversion of water deficit in the tissues which form the joint.

Another aspect of the present invention is the use of an organic glucosamine salt selected from the group consisting of glucosamine glucuronate, glucosamine ascorbate, glucosamine malate, glucosamine hydrogen malate, glucosamine citrate, glucosamine hydrogen citrate, and glucosamine dihydrogen citrate, for the improvement of the joints' functional capacity, elasticity, and flexibility.

Another aspect of the present invention is the use of an organic glucosamine salt selected from the group consisting of glucosamine glucuronate, glucosamine ascorbate, glucosamine malate, glucosamine hydrogen malate, glucosamine citrate, glucosamine hydrogen citrate, and glucosamine dihydrogen citrate, for the preparation of a nutritional supplement for the prophylaxis and reversion of the physical overexertion syndrome in athletes and the undesirable effects associated therewith, particularly bone, joint, muscle, and cartilage injuries.

In a preferred embodiment, the organic glucosamine salt is glucosamine glucuronate, glucosamine ascorbate, glucosamine malate, glucosamine hydrogen malate, glucosamine citrate, glucosamine hydrogen citrate, or glucosamine dihydrogen citrate.

In an equally preferred embodiment, the medicament is adapted for oral administration.

In an equally preferred embodiment, the medicament is adapted for intra-articular administration.

All the uses claimed in the present invention are interrelated in such a way that they form a single inventive concept.

When we speak herein about glucosamine malate, this relates to diglucosamine malate, i.e. the salt that is formed when the two carboxyl groups react.

When we speak herein about glucosamine citrate, this relates to triglucosamine citrate, i.e. the salt that is formed when the three carboxyl groups react.

There are various known procedures for the preparation of glucosamine salts. Some of them consist of previously obtaining the glucosamine base from glucosamine hydrochloride, and subsequently adding the corresponding acid, depending on the salt one wishes to obtain. In general, in order to obtain glucosamine base, glucosamine hydrochloride is treated with triethylamine (L. Rovati, CH 525.861), or with sodium methoxide (L. Rovati, U.S. Pat. No. 3,683,076), or also by means of anionic exchange resins. The salts may also be directly obtained from glucosamine hydrochloride and using an anionic exchange resin previously conditioned with the acid containing the anion of the salt one wishes to produce, or else an acid-metal salt, or they may also be directly produced from glucosamine hydrochloride and an acid-metal salt. If the organic acid contains more than one carboxyl group, by varying the starting quantity of glucosamine or glucosamine hydrochloride, we will obtain the desired salt.

For use in the treatment or prophylaxis of arthrosis, in the treatment of inflammation associated with arthrosis, and in the treatment of pain associated with arthrosis, the salts in the invention are formulated in appropriate pharmaceutical compositions, using conventional techniques and excipients or vehicles, such as the ones described in Remington's Pharmaceutical Sciences Handbook, Mack Pub. Co., N.Y., USA.

The pharmaceutical compositions in the invention may be administered to the patient in required doses. Administration of the compositions may be performed by various means, for example, oral, intravenous, intraperitoneal, intra-articular, subcutaneous, intramuscular, topical, sublingual, intradermal, or intranasal. The pharmaceutical compositions in the invention include a therapeutically effective quantity of the salt in this invention, with said quantity being dependent on many factors, such as, for instance, the patient's physical condition, age, sex, specific compound, means of administration, and other factors well-known in technology. Furthermore, it is understood that said dosage of the active compound may be administered in single- or multiple-dose units in order to provide the desired therapeutic effects. If so desired, other therapeutic agents may be used jointly with the ones provided by this invention.

In general, the pharmaceutical preparations in the invention will be in solid or liquid form, or in the form of a gel. The solid-form pharmaceutical preparations which may be prepared in accordance with the present invention include powders, minigranules (pellets), tablets, dispersable granules, capsules, suppositories, and other solid galenical forms. The liquid-form preparations include solutions, suspensions, emulsions, and microspheres. Preparations in solid form which, immediately before being used, may be converted to liquid preparations for oral, parenteral, or intra-articular administration, are also contemplated. Said liquid forms include solutions, suspensions, and emulsions.

In order to prepare the nutritional supplements to be used in accordance with the invention, the salts in the invention are formulated with appropriate components and excipients used in nutrition. The nutritional supplements may be, for instance, in solid or liquid form, in the form of emulsions or suspensions, or as a gel.

DETAILED DESCRIPTION OF THE INVENTION

Figure 1:
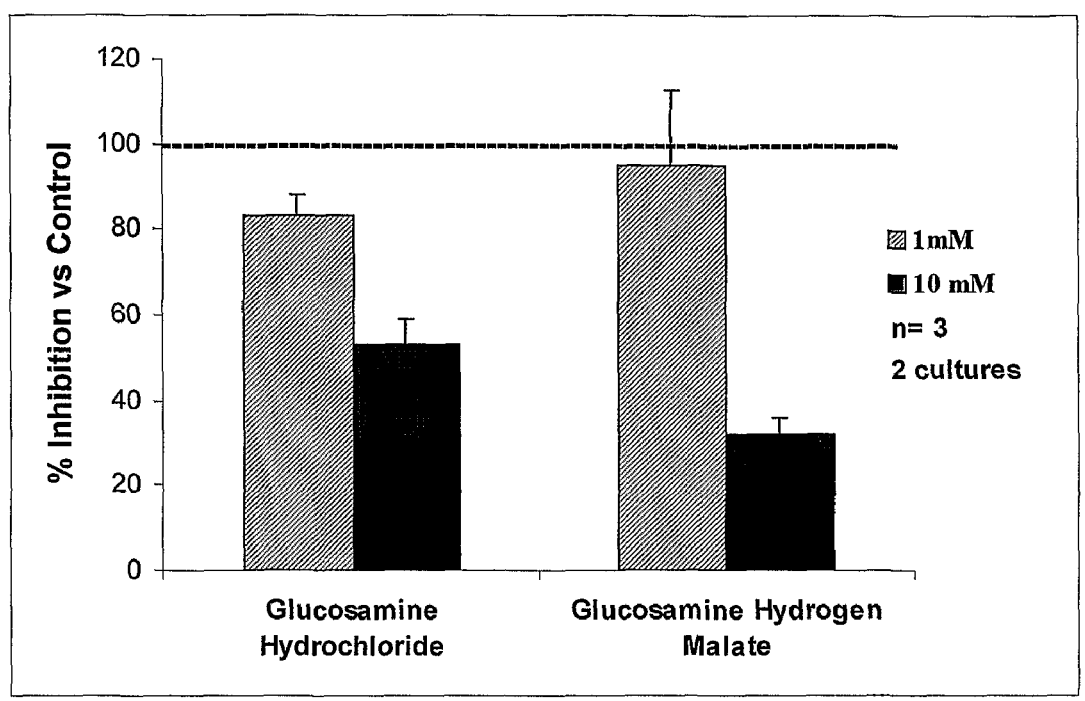
FIG. 1 represents the results of the inhibition of aggrecanolysis induced by IL-1α, both for glucosamine hydrochloride and for glucosamine hydrogen malate with respect to the control. The control represents the culture to which only IL-1 α has been added.

The following examples are merely illustrative and do not represent a limitation on the scope of this invention.

CHEMICAL EXAMPLE

Example 1

Preparation of Glucosamine Hydrogen Malate

Under constant stirring, 1 kg of finely ground glucosamine hydrochloride (preferably 100%<200 microns) was added to 0.77 L of distilled water contained in a three neck flask.

The stirring was continued and, while maintaining the temperature at 10-20° C., 0.562 kg of triethylamine was added for 20-30 minutes. Subsequently, 1.64 L of methanol were added and the stirring was continued for 30 minutes. The product was filtered, and the precipitate was re-suspended in 1.3 L of methanol and was once again stirred for 5 minutes. Subsequently, it was filtered once again. It was then washed with methanol three more times.

Once the product was filtered, it was dried in a vacuum stove at ambient temperature.

737 g of glucosamine base were produced, wherein it was verified that the content of residual chlorides was less than 0.5%.

In order to obtain glucosamine hydrogen malate, the glucosamine base was introduced in a precipitation vessel and 2,948 mL of de-ionized water were added in order to prepare a 25% (w/v) solution. It was stirred until complete dissolution was achieved and, subsequently, 551.6 g of malic acid were slowly added, at a controlled temperature between 2-4° C. (approximately 1 hour).

Once the reaction was finished, in order to obtain the solid product, it was subject to a lyophilisation process; 1,280 g of a white solid were obtained, with a melting point of 132° C. with decomposition.

Richness: 95.4%
Chloride content: 0.3%
Formation of the salt was confirmed by the absence of chlorides.

Example 2

Preparation of Glucosamine Glucuronate

The procedure described in Example 1 was followed, starting from glucosamine base and glucuronic acid.

Melting point: 118° C. with decomposition.
Richness: 94.0%
Chloride content: 0.1%
Formation of the salt was confirmed by $^1$H-NMR and by the absence of chlorides.

Example 3

Preparation of Glucosamine Dihydrogen Citrate

The procedure described in Example 1 was followed, starting from glucosamine base and citric acid.

Melting point: 142° C. with decomposition.
Richness: 94.6%
Chloride content: 0.24%
Formation of the salt was confirmed by $^1$H-NMR and by the absence of chlorides.

The $^1$H-RMN shows a 0.12 ppm displacement of the signal corresponding to the —CH$_2$— whose —COO$^-$ is forming the salt with glucosamine.

Example 4

Preparation of Glucosamine Ascorbate

The procedure described in Example 1 was followed, starting from glucosamine base and ascorbic acid.

Melting point: 135° C. with decomposition.
Richness: 93.8%
Chlorides: 0.4%
Formation of the salt was confirmed by $^1$H-NMR and by the absence of chlorides.

PHARMACOLOGICAL EXAMPLES

Example 1

Determination of Glucosamine Hydrogen Malate's Capacity to Inhibit Aggrecan Degradation Induced with IL-1α

The study of the inhibition of aggrecan degradation was performed on a chondrocyte culture from a rat chondrosarcoma cell line. This cell line, called LTC, deposits an extra-cellular matrix similar to the cartilage's, expresses all the components of the aggrecanase system, generates the fragmentation of aggrecan by said enzymes, and responds to known aggrecanolysis inhibitors such as glucosamine hydrochloride.

This procedure may also be applied to evaluate the effectiveness of glucosamine glucuronate, glucosamine ascorbate, glucosamine malate, glucosamine citrate, glucosamine hydrogen citrate, and glucosamine dihydrogen citrate.

Materials and Methods

The assays were performed on chondrocyte cultures from a rat chondrosarcoma cell line called LTC.

The LTC cells were kept in a monolayer culture in a Gibco DMEM medium (Dulbecco's Modification of Eagle's Medium) (containing 4.5 g/L of glucose) supplemented with sodium bicarbonate (3.7 g/L), glutamine (2 mM), ascorbic acid (50 mg/L), gentamicin (50 mg/L), and bovine fetal serum Hyalone (10%), at pH 7.4.

The confluent LTC cell cultures were trypsinised and 40,000 cells per 0.5 mL of culture were seeded in 48-well plates. They were maintained for 5 days, during which time they deposited 15-30 μg of glycosaminoglycans (GAG) in each well.

The medium was separated, the cell membranes were washed by adding 5×1 mL of a catabolic medium {DMEM+ 4.5 g/L glucose supplemented with sodium bicarbonate (3.7 g/L), glutamine (2 mM), and 10 ng/mL of IL-1α (interleukin-1α) at pH 7.4}. Subsequently, the cultures were kept in 200 µL of this medium, supplemented or not with glucosamine hydrogen malate, for 4 days, without changing the medium, at 37° C.

In order to verify the effect of glucosamine hydrogen malate on aggrecan degradation, a Western Blot was performed.

For the Western Blot, 20 µL of 50 mM tris-acetate at pH 7.3 were added to each well. The cultures (medium+cell membrane) were deglycosylated with 50 mU of chondroitinase ABC at 37° C. for 4 hours. Subsequently, the samples in each well were recovered and centrifuged at 1,460 g for 10 minutes. 25 µL-fractions of the supernatant were separated by electrophoresis (gel gradient 8-12% SDS PAGE) and analysed by means of a Western Blot using anti-G1 antibody. The antiserum was used at a 1:5,000 dilution and the peroxidase-conjugated goat anti-(rabbit IgG) was detected by means of the Amersham ECL Kit. The exposure time ranged between 5 seconds and 5 minutes in order to obtain quantifiable images. The Western Blots were scanned and the bands were quantified by means of the SCION image analysis software. In relation to the described procedure, see: J. D. Sandy et al., *Biochem. J.* 335, 59-66 (1998).

Results

FIG. 1 represents the results of the inhibition of aggrecanolysis induced by IL-1α, both for glucosamine hydrochloride and for glucosamine hydrogen malate with respect to the control. The control represents the culture to which only IL-1α has been added.

The results of inhibition vs. the control are the following:
1 mM glucosamine hydrochloride: 83±4.9%
10 mM glucosamine hydrochloride: 53±5.8%
1 mM glucosamine hydrogen malate: 95±17.5%
10 mM glucosamine hydrogen malate: 32±3.7%

As can be seen in FIG. 1, 10 mM glucosamine hydrogen malate is significantly more effective than glucosamine hydrochloride.

The invention claimed is:

1. A method for treatment of osteoarthritis in a mammal, comprising administering to a mammal in need thereof an organic glucosamine salt selected from the group consisting of glucosamine malate and glucosamine hydrogen malate.

2. The method of claim 1, wherein said method results in treatment of inflammation associated with osteoarthritis in said mammal.

3. The method of claim 1, wherein said method results in treatment of pain associated with osteoarthritis in said mammal.

4. The method of claim 1, wherein the organic glucosamine salt administered is glucosamine hydrogen malate.

5. The method of claim 1, wherein the organic glucosamine salt is orally administered.

6. The method of claim 1, wherein the organic glucosamine salt is intra-articularly administered.

7. The method of claim 1, wherein the organic glucosamine salt is administered in a preparation selected from the group consisting of a liquid, a solid, an emulsion, a suspension, and a gel nutritional supplement.

8. The method of claim 1, wherein the organic glucosamine salt is administered in a nutritional supplement as a chondroprotector.

* * * * *